(12) United States Patent
Koehler et al.

(10) Patent No.: US 7,779,183 B2
(45) Date of Patent: Aug. 17, 2010

(54) COMMUNICATION ADAPTER FOR AMBULANT MEDICAL OR THERAPEUTIC DEVICES

(75) Inventors: Matthias Koehler, Laudenbach (DE); Peter Blasberg, Weinheim (DE); Guenter Handwerker, Boehl-Iggelheim (DE); Manfred Aigner, Heimstetten (DE); Christian Habermann, Haimhausen (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 59 days.

(21) Appl. No.: 11/467,785

(22) Filed: Aug. 28, 2006

(65) Prior Publication Data

US 2007/0055799 A1  Mar. 8, 2007

(30) Foreign Application Priority Data

Aug. 27, 2005 (EP) .................................. 05018651

(51) Int. Cl.
*G06F 13/12* (2006.01)
*A61B 5/05* (2006.01)

(52) U.S. Cl. ........................................ 710/72; 600/407
(58) Field of Classification Search ................... 710/72; 600/407
See application file for complete search history.

(56) References Cited

U.S. PATENT DOCUMENTS

| 6,558,321 | B1 | 5/2003 | Burd et al. |
| 6,564,105 | B2 | 5/2003 | Starkweather et al. |
| 6,577,899 | B2 | 6/2003 | Lebel et al. |
| 6,584,336 | B1 | 6/2003 | Ali et al. |
| 6,635,014 | B2 | 10/2003 | Starkweather et al. |
| 6,912,651 | B1* | 6/2005 | Hamdi et al. .................. 713/1 |
| 7,028,114 | B1* | 4/2006 | Milan et al. .................. 710/100 |
| D522,656 | S * | 6/2006 | Orr et al. .................... D24/169 |
| D542,681 | S * | 5/2007 | Young ......................... D10/80 |
| 7,467,065 | B2 | 12/2008 | Neel et al. |
| 2001/0056226 | A1 | 12/2001 | Zodnik et al. |
| 2002/0178126 | A1* | 11/2002 | Beck et al. ..................... 705/75 |
| 2002/0193679 | A1* | 12/2002 | Malave et al. ............... 600/407 |
| 2003/0032867 | A1 | 2/2003 | Crothall et al. |
| 2003/0163088 | A1 | 8/2003 | Blomquist |
| 2004/0004637 | A1* | 1/2004 | Ghercioiu et al. ........... 345/771 |
| 2005/0113655 | A1 | 5/2005 | Hull |

FOREIGN PATENT DOCUMENTS

WO     WO 98/59487     12/1998

(Continued)

OTHER PUBLICATIONS

Eldon D. Lehmann, 'Database Software for use with Blood Glucose Meters', Nov. 2, 1999, Diabetes Technology & Teherapeutics.*

(Continued)

*Primary Examiner*—Henry W. H. Tsai
*Assistant Examiner*—Hyun Nam
(74) *Attorney, Agent, or Firm*—Eric R. Waldkoetter; Roche Diagnostics Operations, Inc.

(57) ABSTRACT

The invention generally relates to a communication adapter for use with an ambulant medical device. The device carries out a data transmission to the communication adapter that carries out a data transmission to a computer by means of a data connection. The communication adapter processes the data to be read-out from the devices in such a fashion that it can be displayed on a computer without the use of specific software.

36 Claims, 3 Drawing Sheets

FOREIGN PATENT DOCUMENTS

| WO | WO 00/18449 | 4/2000 |
|---|---|---|
| WO | WO 2005/009514 A2 | 2/2005 |
| WO | WO 2005/083619 A2 | 9/2005 |

OTHER PUBLICATIONS

Garg et al. 'Improved Glucose Excursions Using an Implantable Real-Time Continuous Sensor in Adults with Type 1 Diabetes', Mar. 2004, Diabetes Care.*

Definition of 'memory resident' from www.credoreference.com, 2008, Helicon Publishing.*

Merrit, Rick et al., "Wireless Hospital, Health Care Products On The Upswing", TechWeb, pp. 1-2; Jan. 7, 2004; URL: http:/www.techweb.come/wire/26803705; (XP-002348225).

Steinfeld, Edward F., "Internet-appliance technology automate test equipment", EDN, pp. 157-169; Oct. 12, 2000; URL: www.ednmag.com; (XP-001143050).

Corresponding European Search Report dated Feb. 2, 2007.

* cited by examiner

COMMUNICATION ADAPTER FOR AMBULANT MEDICAL OR THERAPEUTIC DEVICES

REFERENCE TO RELATED APPLICATIONS

The present application is based on and claims priority to European Patent Application No. 05 018 651.9, filed Aug. 27, 2005, which is hereby incorporated by reference in its entirety.

TECHNICAL FIELD

The invention generally relates to a communication adapter for use with a portable ambulant-operable medical or therapeutic device, in particular a device for the diagnosis or treatment of a disorder of glucose metabolism.

BACKGROUND

Installed between the medical or therapeutic device and the computer, a communication adapter of this type can transmit data from the device to the computer in order to display operating parameters or measuring data of the device by means of the computer, if the communication adapter is also provided for the transmission of data from the computer to the medical or therapeutic device, the device can also be operated by means of the computer, for example in order to configure the device of trigger certain actions of the device.

Accordingly, the medical or therapeutic device comprises a device processor for controlling the device and a device-adapter interface for the communication of the device processor with the communication adapter. The communication adapter comprises an adapter processor for controlling the communication adapter, an adapter-device interface for the communication of the communication adapter with the device, an adapter-computer interface for the communication of the adapter processor with a computer interface of the computer, and a device driver with corresponding transmission protocol for the communication with the device.

The devices that are capable of exchanging data with a computer through a communication adapter according to the invention usually can be operated independent of mains power. The invention is aimed mainly at devices for the diagnosis or treatment of a disease, in particular a disorder of glucose metabolism such as diabetes. It is therefore related to analytical measuring devices for determining or recording (so-called "electronic diaries") a medically significant parameter, in particular a blood glucose meter, a blood sugar measuring device, a cholesterol measuring device, a blood coagulation parameter measuring device, a blood pressure measuring device, a device for measuring the body weight, a blood glucose recorder or a blood pressure recorder or devices for injection of a medical agent into a body, in particular an insulin pump. It is particularly preferred according to the invention to use medical or therapeutic devices that function and can be operated independently, i.e. independent of other components or devices being connected, i.e. in particular, independent of the communication adapter. This means that, for example, a measuring device delivers measuring values or an insulin pump works with being connected to the communication adapter or other device.

A blood glucose meter is a blood glucose measuring device that can be used to determine the blood glucose content. For this purpose, it is customary to generate a puncture wound in a body, draw a drop of blood, and use the blood glucose measuring device to determined the blood glucose content of the drop. However, it is also conceivable to measure the blood glucose by means of a continuous measurement, for example with sensors introduced into the body or through the skin.

Insulin pumps are small infusion devices that are carried on the body and administer insulin to the body continuously or intermittently using a catheter and a needle placed under the skin. In the process, the dosage can be adapted to a certain daily rhythm or certain events, such as the ingestion of meals.

Blood glucose recorders are devices that record blood glucose concentrations for a predetermined period of time, for example, in order to be able to determine a suitable insulin dosing scheme for a diabetes patient.

In the following, the invention shall be described on the basis of such devices for the diagnosis or treatment of a disorder of glucose metabolism without limiting the general applicability of the invention.

A communication adapter that receives data from a medical device via an infrared interface and sends data to a central database via the Internet is known from the document WO 98/59487. For this purpose, the communication adapter is connected to the keyboard interface of a computer with Internet access. The communication adapter converts the data received from the device into keyboard commands such that the computer sends the data to a central database. The central database then processes the data received and returns the data to the computer to which the communication adapter is connected for display by means of an Internet browser. A disadvantage of this system is that the user must disconnect the keyboard from the computer such that the computer can no longer be operated while the communication adapter is connected. Another disadvantage is that the data read-out from the device by means of the communication adapter can be displayed exclusively by means of a computer with Internet access and even then only if the Internet connection is actually established.

From the document WO 00/18449, a stand with integrated infrared ports is known, into which a blood glucose meter or an insulin pump can be inserted in order to exchange data with the stand. In the process, the user must select the adequate communication protocol for the inserted device by means of a switch. The shape of the stand and the position of the infrared ports therein must match the contour of the device to be inserted. Consequently, it is not possible to read-out devices of any arbitrary shape, but only certain devices, whereby the infrared ports must be arranged at the proper locations. Newly developed devices often have a changed design and cannot be read-out with the stand for mechanical reasons due to the changed shape of the new housing and possible alternatives placement of the infrared ports. For this reason, the stand is suitable for use with future, newly developed devices only to a very limited degree. Moreover, another disadvantage is that the stand must be set by hand to each device in order to facilitate the communication.

The document U.S. Pat. No. 6,564,105 B2 describes a communication protocol for an implanted medical device, for example an infusion pump.

The document US 2003/0163088 discloses an infrared interface in a computer or in an external station exclusively for programming insulin pumps.

From document US 2003/0032867, it is known to store blood glucose measuring values jointly with a time and a date stamp in a single protocol. The corresponding patient data are stored in an additional protocol. The separate storage in different protocols leads to an increase in the effort required when the data is to be combined, e.g. in patient files at the hospital or doctors office.

A medical system with an ambulant medical device, such as a blood glucose meter or an insulin pump, is known from the family of patents of U.S. provisional patent application Ser. No. 60/177,414, Medical Research Group Inc. (e g. U.S. Pat. No. 6,577,899 and U.S. Pat. No. 6,635,014), in which the device comprises a telemetry unit that communicates with a telemetry unit of a communication device for read-out of data and for programming of the devices.

From document WO 2005/0836190 A2, which was published after the prior date of the present application, is known a network for communication with medical devices, in which a communication server is used. An Internet or the Internet is required in order to establish the connection to the medical device, and a "remote device" in addition to the medical device is required to control the connection.

The document US 2005/0113655 A1 relates to a pulse oximeter device, in which a sensor sends the raw data by means of a wireless transmission to the pulse oximeter device, the pulse oximeter processes the measured raw data by means of a processor, and then sends it in wireless fashion to a receiver for display in the form of a web page. In this context, each pulse oximeter requires its own software for processing and displaying the data as well as its own corresponding device integrated hardware components for transmission of the data.

The document U.S. Pat. No. 6,584,336 B1 describes a communication adapter (docketing station) for connecting a pulse oximeter device to a computer interface. The connections of the communication adapter both to the pulse oximeter device and to the computer interface are wire-based such that the shape of the communication adapter and the position of the plug-in connection must be adapted to the contour of the device inserted therein. Consequently, it is not possible to read-out devices of any arbitrary shape, but only certain devices using the communication adapter.

The document WO 2005/009514 A2 discloses; a communication system for connecting an implantable medical device to various peripheral facilities by means of a programming facility that is connected to the medical device by means of wireless data transmission.

The document U.S. Pat. No. 6,558,321 B1 describes a communication adapter (docketing device) for connecting a medical device to a computer interface. The data transmission between the medical device and the computer can proceed in both directions.

The document US 2001/0056226 A1 describes a recording facility for recording data of medical measuring devices and for transmitting the data via a network to a monitor.

SUMMARY

Based on the prior art as described, one of the object underlying the invention is to create a communication adapter for transmitting data between a medical or therapeutic device and a computer that is more versatile in use and easier to operate by the user.

Accordingly, a communication adapter according to the invention for use with a portable, ambulant-operable medical or therapeutic device in particular a device for the diagnosis or treatment of a disorder of glucose metabolism, for transmitting data between the medical or therapeutic device and a computer that serves for displaying operating parameters or measuring data of the device and/or for operating the device, wherein the medical or therapeutic device comprises a device processor for controlling the device and a; device-adapter interface for the communication of the device processor with the communication adapter, and wherein the communication adapter comprises an adapter processor for controlling the communication adapter, an adapter-device interface for the communication of the communication adapter with the deices an adapter-computer interface for the communication of the adapter processor with a computer interface of the computer, and a device driver with corresponding transmission protocol for the communication with the device.

The communication adapter comprises the soft- or firmware required for processing the data read-out from the device independent of the computers and providing the data in a data format that can be displayed by the computer with standard display software for read-out by the computer via the adapter-computer interface for the display of the data on the computer.

If the communication adapter has the capability, i.e. the requisite soft- or firmware, for processing of the data for display with a standard display software of the computer, no special additional program in the computer for displaying the data is required. The data format generated by the communication adapter for displaying the date read-out from the device by the computer is a format that can be displayed by an Internet browser or an HTML or XML format that can be displayed by means of HTML or XML display software.

A soft- or firmware for read-out from the devices and processing of the data is provided in the communication adapter. The communication adapter transmits the data in a format that can be displayed by an Internet browser, e.g. as an HTML file, to the computer when the computer reads-out the data from the communication adapter. The computer uses a standard program to display the data in the form of graphs, statistics and tables on the monitor of the computer. A standard program in this context shall be defined as a program that would also be installed on a computer not intended for use with a communication adapter according to the invention. Internet browsers, such as, for example, Internet Explorer, Netscape or Mozilla, are standard programs according to the invention.

Usually, an Internet browser of this type is installed as part of the standard software of a computer, whereby the various common Internet browsers are designed such that they can process the same data format, in particular an HTML data format, for compatibility reasons.

The communication adapter serves for temporary storage of the data or HTML data received from the device. For read-out of the data, the communication adapter is controlled by means of monitor, mouse, and keyboard of the computer. Accordingly, the computer only serves as user interface for displaying the data and operating the communication adapter without specific software having to be installed or started-up on the computer for this purpose. For data protection reasons, it is advantageous when thereupon none of the data read-out from the device and/or the communication adapter is stored on the computer in the process.

In another embodiment, the communication adapter for use with a portable, ambulant-operable medical or therapeutic device, in particular a device for the diagnosis or treatment of a disorder of glucose metabolism, for transmitting data between the medical or therapeutic device and a computer that serves for displaying operating parameters or measuring data of the device and/or for operating the device, wherein the medical or therapeutic device comprises a device processor for controlling the device, and a device-adapter interface for the communication of the device processor with the communication adapter, and wherein the communication adapter comprises an adapter processor for controlling the communication adapter, an adapter-device interface for the communication of the communication adapter with the device, an adapter-computer interface for the communication of the adapter processor with a computer interface of the computer, and a device driver with corresponding transmission protocol for the communication with the device.

The control of the communication adapter by the computer is implemented such that read commands are sent from the computer to the communication adapter by means of which trigger files are read in the communication adapter that are interpreted as control commands for the communication adapter by the soft- or firmware of the communication adapter.

Read commands are sent from the computer to the communication adapter preferably via the computer interface of the computer to the adapter-computer interface of the communication adapter.

The command control of the communication adapter is implemented via read commands (links) to the storage medium of the communication adapter. Upon a link being clicked on the monitor, one or more certain so-called trigger files on the communication adapter are read and the reading of a file of this type is interpreted by the soft- or firmware of the communication adapter as a certain command, e.g. "Print" or "Read device". By this means it is feasible to control the communication adapter by the computer using a software that is installed on the computer as a standard, such as, for example, an Internet browser, without a particular software program capable of executing commands being installed on the computer.

The use of an Internet browser for displaying the read-out data and controlling the communication adapter, it must also be taken into consideration that standard, Internet browsers cannot be used to send write commands to a computer in order to prevent such commands from starting-up the automatic copying or deleting of files present on the computer, for example when opening an Internet page. Consequently, especially in as far as fit concerns the use of Internet browsers, the reading of trigger files for controlling the communication adapter from the computer is advantageous.

In practical application it is advantageous for the trigger for a command to consist of the reading of multiple files, preferably in different directories on the communication adapter, either simultaneously or in a fixed sequence. By this means it is feasible not only to increase the degree of coding of potential commands, but also to increase the security, for example in order to prevent commands being sent inadvertently to the communication adapter while scanning the communication adapter with a virus scanner or while viewing the content of the communication adapter with another program, for example a Windows Explorer.

The adapter-device interface for the communication of the communication adapter with the device is an interface for wireless data transmission, for example an infrared interface a Bluetooth interface or an RF interface. Accordingly, the device-adapter interface for the communication of the device processor with the communication adapter is also an interface for wireless data transmission for example an infrared interface, a Bluetooth interface or an RF interface.

In principle, the adapter-device interface can be implemented in any fashion, in the case of wire based data transmission the user of the device must have available and connect a matching connection cable in order to establish the communication of the device with a communication adapter. This may be difficult, especially in the case of ill individuals. Moreover, the plug connection contacts may get contaminated or damaged. For this reason, wireless communication between the device and the communication adapter, is preferred.

In contrast, the adapter-computer interface for the communication of the adapter processor with the computer interface of the computer and, accordingly, the computer interface of the computer preferably is each an interface for wire-based data transmission. In customary computers, it is not common to provide an interface for wireless communication at the factory, whereas the installation of interfaces for wire-based communication, for example of an USB interface is standard. However, wireless communication between computer and communication adapter can also be advantageous, for example in the form of a WLAN connection.

The use of a wire-based interface for data transmission between communication adapter and computer thus extends the application range for a user. In, this context, it is not disadvantageous to the user in many applications that a cable connection must be established between computer and communication adapter, for example when the user of the device does not carry the communication adapter with him, for example when the user takes his device to a read-out station on which a communication adapter is already connected to a computer, such as, for example, in a pharmacy or doctor's office.

The communication adapter comprises a plurality of device drivers with corresponding transmission protocols that are automatically queried in the case of a device communicating with the communication adapter via the adapter-device interface in order to select from the plurality of device drivers an adequate device driver for the device on hand. A communication adapter can then be used as an additional device in conjunction with a plurality of medical or therapeutic devices or times of such devices. The medical or therapeutic devices do not need to be equipped with hard or software components providing the function of the communication adapter and can therefore be manufactured more easily. The communication protocol for various devices can be different also, provided the prerequisites for the use of the same hardware are met. For example, some devices can use a proprietary communication standard and others a general IrDA standard.

The trials of the device drivers for establishing a communication with a device is started-up automatically as soon as the communications adapter is supplied with electrical power. The trials can also be continued when a device has been recognized in order to check if any additional devices to communicate with simultaneously if needed, are present, or the trials can be started-up again if a communication connection to a device gets interrupted in order to re-establish the connection to this device or newly establish the connection to a different device. These automatic processes simplify the use of the communication adapter by a user or, in particular, by changing users or upon the use of different devices.

By this means, a device to be read-out by the communication adapter, for example a blood glucose meter an insulin pump or an electronic diary for blood glucose values, can be recognized automatically by the communication adapter. Devices such as those for the diagnosis and treatment of a disorder of glucose metabolism usually have an infrared interface for external communications but the protocols and sets of commands used in each individual case differ. For this reason, the soft- or firmware of the communication adapter comprises the device drivers possible that include the corresponding sets of commands. While the communication between the communication adapter and the device is being established, the communication adapter uses the communication protocols (drivers) stored in it to sequentially query the in initially unknown device until it finds the adequate communication protocol that allows the communication with the device to be implemented. From then, the communication proceeds with the driver thus found.

In the process, it is advantageous to also optimize the transmission rate (baud rate). For this purpose, the communication adapter, for example, queries the device at a low initial or default transmission rate to determine which transmission rate the device is capable of implementing and then switches to the highest common transmission rate.

However, by this means it is not only feasible to recognize an initially unknown device, but also to communicate with future, newly developed devices provided the same type of communication, for example an infrared or radio, e.g. bluetooth interface, is used. It may be necessary to load a new software diver onto the communication adapter in this case. A software update of this type can be implemented, for example, via a download of a driver file provided by the manufacturer on the Internet or by means of a CD, when the communication adapter is connected to a computer. Accordingly, the communication adapter is capable of being updated for the communication with new devices or changed device software.

The search for the adequate device driver upon activation of the communication of the communication adapter with a device can be optimized by initially starting-up the communication using the device driver most recently recognized to be adequate, or pair of device drivers consisting, for example, of blood glucose meter and insulin pump or using the most recently used driver more frequently than the others in the testing of device drivers to establish communication. This allows the communication between the communication adapter and the device to be established more rapidly in the common applications of the devices of a user.

The communication adapter can, in addition, be provided to generate the data read-out from the device in a data format that can be stored and store this data in at least one file in the communication adapter from where it can be read-out by the computer via the adapter-computer interface. The communication adapter can also in this embodiment operate in a stand-alone mode, but generates the data not only, for example, as an HTML file for display by an Internet browser but additionally, for example, as XML file which can then be imported into a database or table, for example an Excel table.

For this purpose, a standard software or a firm-specific software is stored on the computer that can import, process the data and use the data to generate the display or stores the data in a database. The communication adapter generates this data independently, despite being connected to the computer like a passive device, for example like an USB device or mass storage device, such as a memory stick. By logging-off and logging-on, the communication adapter can trigger the computer to reload the file system of the communication adapter, and jointly with the firm-specific software, the communication adapter serves as an "intelligent cable" for processing the data read-out from the device.

These and other features and advantages of the present invention will be more fully understood from the following detailed description of the invention taken together with the accompanying claims, it is noted that the scope of the claims is definitely by the recitations therein and not by the specific discussion of the features and advantages set forth in the present description.

BRIEF DESCRIPTION OF THE DRAWINGS

The invention is illustrated in the following based on exemplary embodiments that are shown in the figures. The particularities described therein can be used separately or in combination in order to create preferred embodiments of the invention. In the figures.

In order that the invention may be more readily understood, reference is made to the following examples, which are intended to illustrated the invention, but not limit the scope thereof.

DETAILED DESCRIPTION

The following description of the preferred embodiment is merely exemplary in nature and is in no way intended to limit the invention or its application or uses.

Figure 1:
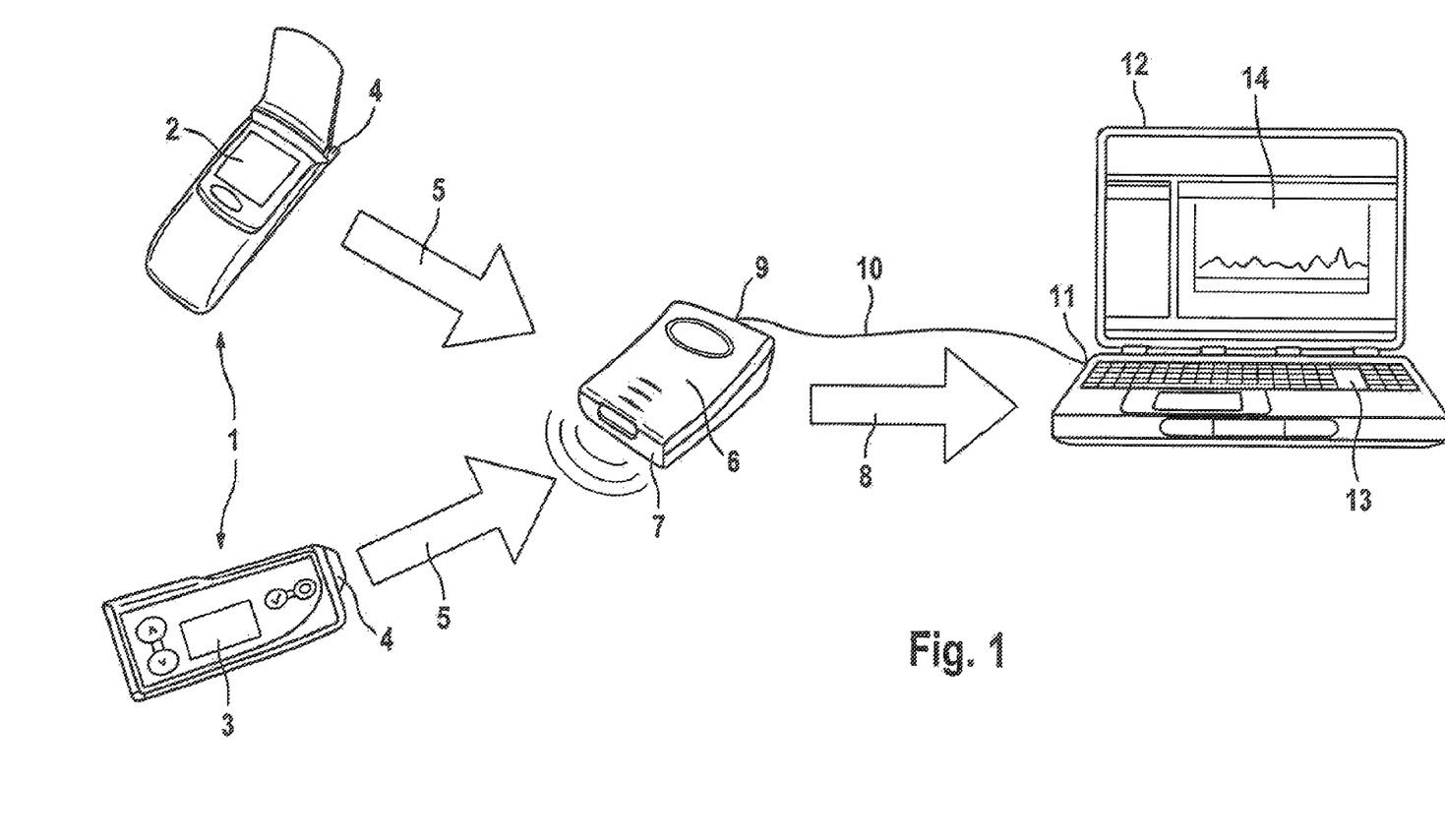
FIG. 1 shows a communication adapter for reading-out data from devices and controlling the communication adapter by means of transmitting trigger files from a computer to the communication adapter.

FIG. 1, shows two portable medical devices 7 that are ambulant-operable without depending on mains supply, namely a blood glucose meter 2 and an insulin pump 3 that are used by a user, possibly in combination. Both devices are provided with a device-adapter interface 4 for sending and/or receiving data which interface is provided in the form of an infrared interface. In the exemplary embodiment shown in FIG. 1, the infrared data transmission 5 is implemented by sending data from the device-adapter interface 4 of the device 1 to a communication adapter 6 that comprises an adapter-device interface 7 for sending and/or receiving data and is also provided in the form of an infrared interface. Connection of device 1 via the device-adapter interface 4 to the adapter-device interface 7 of the communication adapter 6 is preferably implemented in the form of a direct wire-supported or direct wireless (radio or infrared) connection and not by means of a network or a server and/or web server (Intranet or Internet) in order to assure that the communication is simple, secure and direct.

The communication adapter 6 can be provided in the form of a stand-alone device. For wire-based data transmission 8, it is connected through an adapter-computer interface 9 and a transmission cable 10 to a computer interface 11 of a computer 12. The computer 12 can, for example, be a personal computer, a laptop, a handheld computer or the computer in an Internet café, in a doctor's office or in a pharmacy to which the user of the devices 1 goes with his device 1 only or with his device 1 and a communication adapter 6. If the user visits a facility equipped with a computer 12 with standard display software and a communication adapter 6 that is designed for many types of medical and therapeutic devices, for example a suitably equipped pharmacy, there is no need for the user to bring along a computer 12 or communication adapter 6 in order to display the data std in his device. If the user brings along a communication adapter 6, he can also display his date on any arbitrary computers 12 comprising standard display software, for example, in an Internet café.

A wire-based computer interface 11 of the computer 12 can, for example, be a serial interface, a parallel interface, a firmware interface or, preferably, a USB interface. The transmission cable 10 and an adapter-computer interface 9 on the communication adapter 6 are selected to match. If applicable, a communication adapter 6 can comprise multiple wire-based interfaces of various standards. The USB interface is preferred since it is very common, requires little space, and facilitates rapid data transmission. Wireless communication between communication adapter 6 and computer 12 can also be advantageous, for example in the form of a WLAN connection.

For reading-out the data of the devices 1 and displaying the data on the monitor 14 of the computer 12, the communication adapter 6 is first connected to the computer 12 by means of the cable 10. The communication adapter 6 comprises no intrinsic or internal power supply and is supplied with power by the computer interface 11 of the computer 12 via the cable 10. This is advantageous to the user in that the communication adapter 6 can be small and light-weight since no intrinsic power supply is required and no storage batteries or batteries increasing the space requirements and weight thereof need to be contained therein and carried along.

Upon connection of the communication adapter 6 to the computer 12, the communication adapter 6 automatically switches to search mode in which it searches for devices 1 capable of communicating with its adapter-device interface 7. Alternatively the communication adapter 6 can be provided to be switched to search mode by an action of the user, for example by pressing a key.

In case the device-adapter interface 4 of the device 1 is an infrared interface it should be aligned with the adapter-device interface 7 of the communication adapter 6, which in this case also is an infrared interface, in order to facilitate optical data transmission. The communication adapter 6 scrolls through the device drivers stored in it and searches for an adequate device 1 that is capable of communicating with it.

The device-adapter interface 4 on the device 1, in particular an infrared interface, is advantageously activated by manual actuation by the user on the device 1 in order to establish the communication with the communication adapter 6 and then facilitate data transmission or infrared data transmission 5. Manual activation of the device-adapter interface 4 allows the interface to be switched off during all other uses of the device 1 for power saving and data protection reasons.

Once the computer 12 recognized the connected communication adapter 6 and the communication of the communication adapter 6 with the device 1 is established the user can use the keyboard 13 of the computer 12 to call-up an Internet browser and display the data read-out from the device 1 on the monitor 14 by means of the Internet browser without special, specific or individual programming of the computer 12 being required. The user of the device 1 and communication adapter 6 can thus display and view the data on any computer 12 on which an Internet browser is installed without having to install on the computer 12 a specific software for read-out of the communication adapter 6.

This is made possible by the communication adapter 6 comprising the requisite soft- or firmware for processing and displaying the data read-out from the device 1 independent of the computer 12 and sending this data via the adapter-computer interface 9 to the computer 12 using a data format that can be displayed by the computer 12 with standard display software, or providing this data for read-out by the computer 12.

A different independent or additional aspect according to the invention is also illustrated in FIG. 1, according to which the communication adapter 6 is controlled by the computer 12 in that read commands are sent from the computer 12 to the communication adapter 6 by means of which trigger files in the communication adapter 6 are read and interpreted as control commands for controlling the communication adapter 6 by the soft- or firmware of the communication adapter 6.

Since the soft- or firmware required for displaying the data is present in the communication adapter 6 and the computer 12 only serves as display and operating element that requires just a standard display software, i.e. a display software that is part of the standard programs commonly installed on a computer and thus is very widely used, the use of the communication adapter 6 for displaying the data is independent of which computer 12 is used. A standard display software of this type can, for example, be a program that is usually a component that is provided to the user as component of or in conjunction with the operating system software of the computer, or a widely used display software, for example an Internet browser or a HTML or XML display software. This allows the user to be highly mobile in his use of the communication adapter 6 since the communication adapter 6 can be connected to any computer 12, for example while travelling. This is a Real Plug & Play system, it requires only that a connection between communication adapter 6 and computer 12 is established, for example a USB connection by means of the transmission cable 10, and then the data of the devices 1 can be displayed on the computer 12. No administrator rights are needed for this purpose, such that the communication adapter 6 can be used even in the case of computers on which the installation of additional software by a user is blocked.

The "embedded system" is secure with regard to viruses, since the computer 12 serves as user interface only and since the user is familiar with this user interface due to being familiar with the operation of an Internet browser, a keyboard, a mouse, and a monitor, the operation is very easy to learn for the user.

The use of the computer 12 for displaying the data read-out from the devices 1 is associated with many advantages for the user as compared to viewing the data on the display elements of the devices 1. The compact devices 1 have only small display elements capable of displaying only little information at low resolution, in a small format, and usually individual values only. A more sophisticated display or analysis of the data is not feasible or only with much difficulty in contract the monitor 14 of the computer 120 can display the data lavishly and in a processed fashion in graphs or lists and allows for a trend analysis. In general, it can therefore be advantageous for the device 1 and the communication adapter 6 to be provided for transmission of operating data or measuring values of the device 1 from the device 1 to the computer 12 by means of the communication adapter 6, whereby this concerns operating data and measuring values for time points in the past, in this case, no current data or not only current, data, but also, for example, stored measuring values, i.e. histories, are transmitted to and displayed by the computer 12, in particular in the diagnosis or treatment of disorders of glucose metabolism, the past course of operating data and measuring values is of medical and therapeutic interest.

The user can adapt the display on the monitor 14 even in cases, in which the data transmission, for example the infrared data transmission 5, proceeds only from the device 1 to the communication adapter 6, but not from the communication adapter 6 to the device 1. For this purpose, various fixed display variations can be stored in the communication in adapter 6 to be called-up alternatively on the computer 12 by the user.

However, aside from graphically displaying measuring data, profiles, patterns, trends, incorrect behavior, and incorrect dosages, the computer 12 can also display device parameters, such as the serial number of the device 1 that was read-out or a patient identification. Unlike XML data, which is additionally or alternatively read-out with a different software, the HTML data thus read-out is preferably stored on the communication adapter 6 only, as a standard, and deleted on the communication adapter 6 upon severing the adapter-computer interface 9 from the computer interface 11, which protects confidentiality particularly when the communication adapter 6 is used on public-access computers 12, for example in a doctor's office or in a pharmacy to which a user goes with his device 1 in order to read-out the data on a communication adapter 6 provided in these places. Alternatively, it is also feasible to provide a reset button on the communication adapter 6 or a reset icon on the monitor 14 for operating the communication adapter 6 in order to provide for manual deletion of the data on the communication adapter 6.

For reasons of confidentiality the data read-out from the device 1 to be stored in the communication adapter 6 in a volatile memory or to be deleted upon severing of the data transmission connection to a device 1, upon connection of a new device 1 to the communication adapter 6, by pressing a reset button on the communication adapter 6 or by clicking on a reset button on the monitor 14.

Additionally, it can be provided that the display software is a software that can read-out from the communication adapter 6 the data to be displayed by the computer 12, but cannot change this data on the communication adapter 6 or the device 1 such that the data read-out from the device 1 by the computer 12 are transmitted to the computer 12 for temporary display only in that the display software can read-out the data from the device 1 but cannot delete or change the remaining data on the communication adapter 6 or the data of the device 1 remaining on the device 1.

In this case, the data is not stored on the computer 12, but only displayed temporarily by the computer 12 using standard display software. This is similar to opening a text file with a text processing program, whereby the text file can be read from the corresponding storage medium, but remains on the storage medium and is present on the computer only temporarily while it is read and processed. Accordingly, in the invention, the computer 12 accesses data on the communication adapter 6 using its display software, but the data remains on the communication adapter 6.

Because of their wide availability, Internet browsers are particularly well-suited software for this purpose, since they usually are installed as a standard on a computer, utilize standardized transmission protocols and data formats, and reasons related to security standards allow only the reading of data, but not the writing of data and/or no change, deletion or over-writing of the read data, i.e. read-in data only for temporary display on the computer 12 and do not transmit data to the communication adapter 6.

In some cases, it can be provided that the user communicates online on the computer 12 with a web server or host computer, for example on a web site of the manufacturer of his device 1, and that this web server communicates with the communication adapter 6 that is connected to the computer 12. This allows, for example, an update of the soft- or firmware of the communication adapter 6 and/or the device 1 to proceed.

Figure 2:
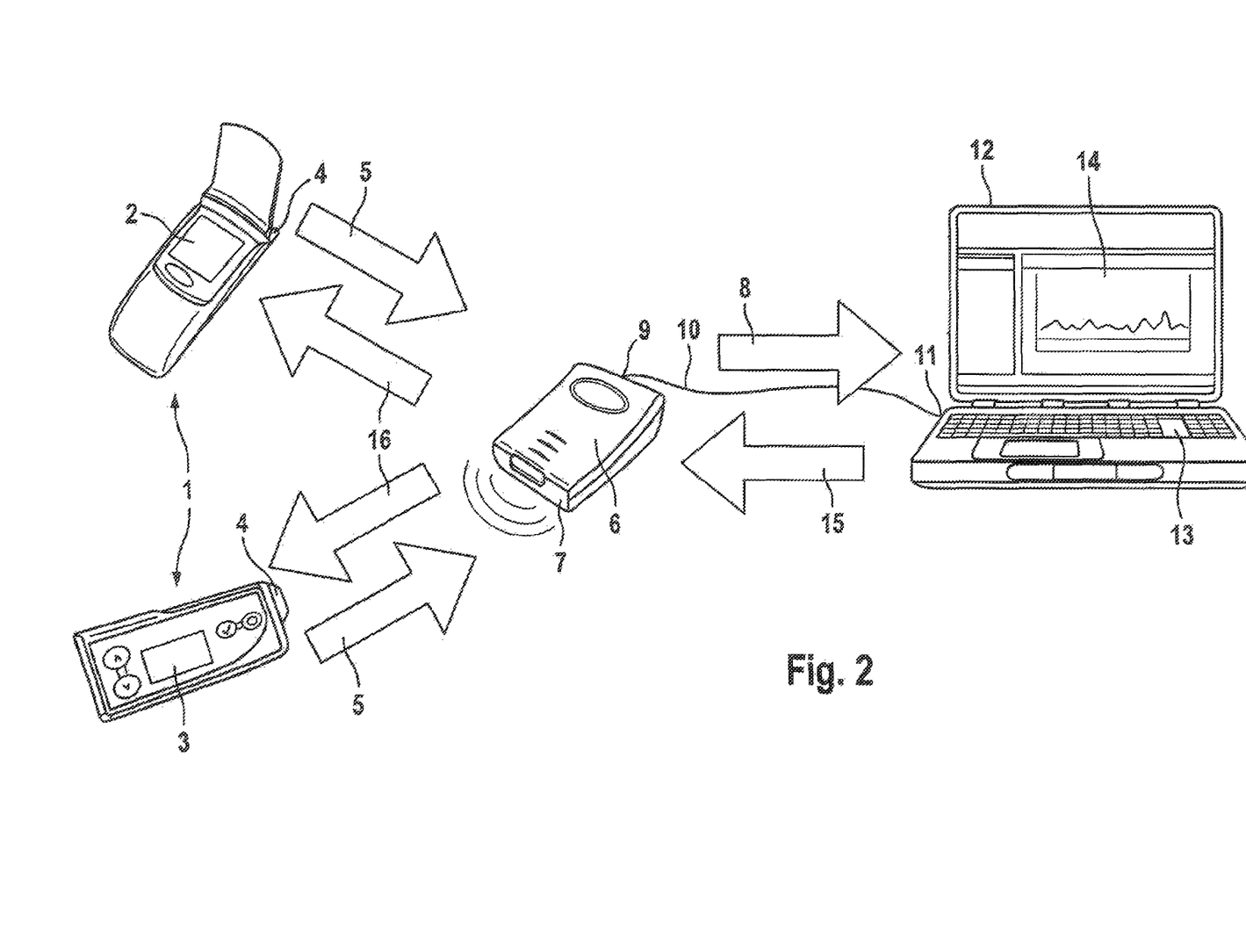
FIG. 2 shows a communication adapter for reading-out data from devices and for operating the devices by means of a computer.

FIG. 2 shows a further exemplary embodiment in which a bidirectional data transmission is used. It corresponds to that of FIG. 1 whereby an additional functionality is provided, namely in that the communication adapter 6 is provided for transmitting data to the device 1 for controlling or programming the device 1 from the computer 12, whereby the controlling or programming of the device 1 from the computer 12 proceeds via the computer interface 11 of the computer 12 to the communication adapter 6 and from the communication adapter 6 via the adapter-device interface 7 of the communication adapter 6 to the device 1. Therefore in the embodiment shown in FIG. 2, also a wire-based data transmission 15 proceeds from the computer 12 to the communication adapter 6 and an infrared data transmission 16 proceeds from the communication adapter 6 to the device 1.

In this case, the communication adapter 6 serves basically as an "intelligent cable" or USB-to-IR adapter. The communication adapter 6 converts the data from the USB protocol to the IR protocol and vice versa. In this case, an additional specific software with the device drivers, e.g. for the data analysis, can be stored on the computer 12 or the computer software utilizes the device drivers and the data read-out as provided by the communication adapter 6. The actual communication with the device 1 is provided by the firmware in the communication adapter 6. The data tan be read-out from the devices 1 by means of the data transmissions 5 and 8 and displayed on the computer 12. Moreover the devices can also be operated, programmed or set by means of the data transmissions 15 and 16. This allows, for example, to set the date and time of day in a blood glucose meter 2 or to set the date and time of day in an insulin pump 3, and to set a certain basal rate time profile.

Figure 3:
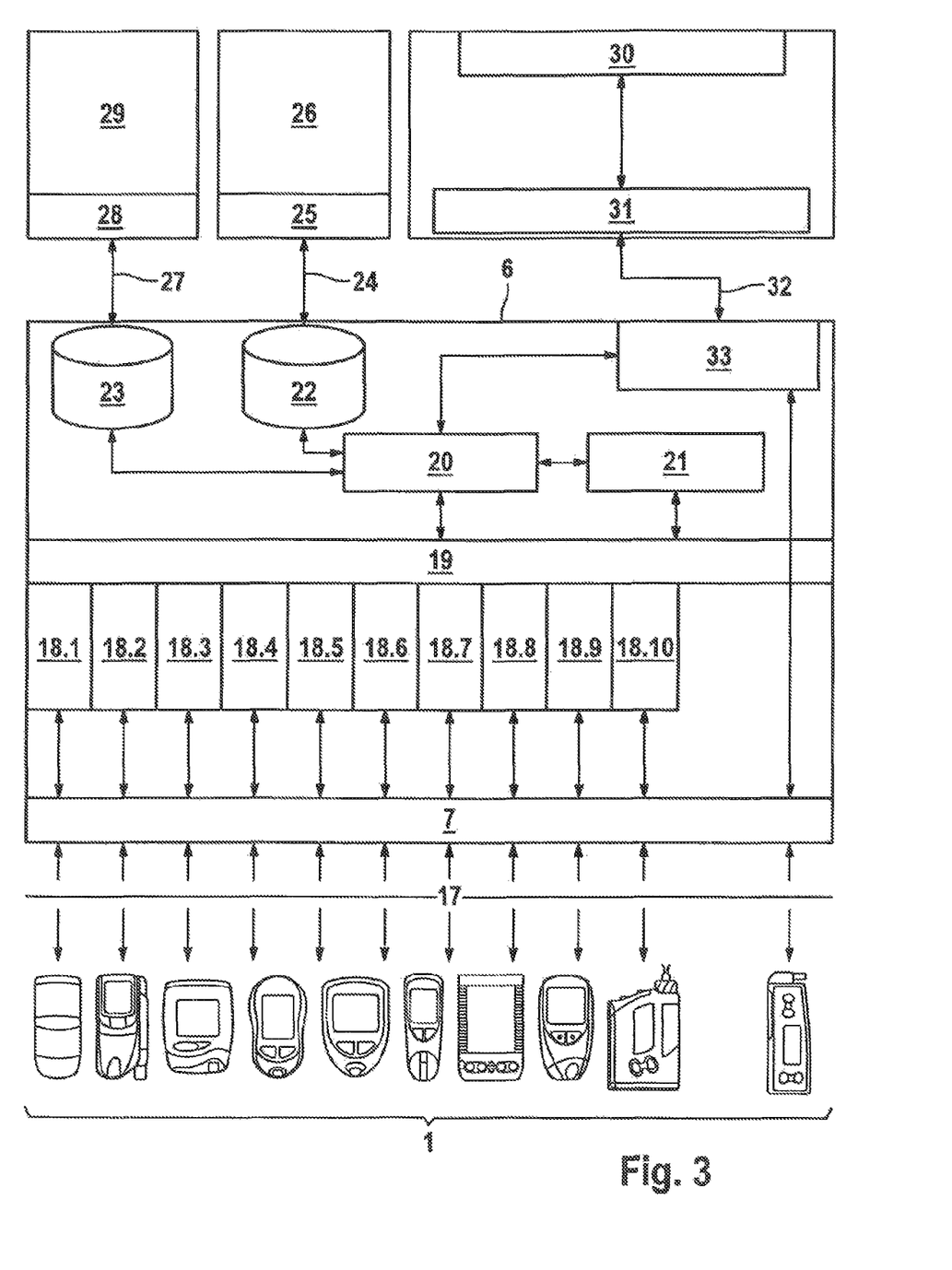
FIG. 3 shows a schematic structure of the process control of a communication adapter with corresponding system, environment.

FIG. 3 shows details of an implementation of a communication adapter 6 to which numerous different devices 1 can be connected. The devices 1 communicate with the adapter-device interface 7 of the communications adapter a by means of device-specific low level device interfaces 17. The communication adapter 6 comprises, a plurality of device drivers that facilitate the device-adapted communication with the devices 1 by means of different protocols 18.1 to 18.10. The universal file manager 19 controls the data processing 20 of the processor and of the data storages 21 in the communication adapter 6. The data output is implemented in the form of HTML reports 22 or in the form of XML data 23. The HTML reports 22 are displayed on an Internet browser 26 of a computer 12 by means of read commands 24 and the data access 25. The XML data 23 is provided to other PC applications, e.g. Excel, of the computer 12 by means of a read command 27 and a data access 28.

In addition, there is a consolidated functionality 30 of a human interface device driver 31. This driver generates read and write, commands 32 in relation to an USB-IR command converter 33 for the control of hardware and the execution of commands.

A communication adapter 6 provides, amongst others, the following advantages mentioned above to the user, (i) Data analysis of data recorded from a device 1 is feasible without having to have and install a specific software. (ii) The device 1 can be recognized by the communication adapter 6 automatically which simplifies its operation. (iii) the wire-based adapter-computer interface 9, the communication adapter 6 does not need to have an intrinsic power supply, (iv) the command control of the communication adapter 6 is implemented by means of reading-out trigger files on the communication adapter 6 from the computer 12 via the adapter-computer interface 9.

A communication adapter 6 facilitates simple and efficient communication between devices 1 on one side, for example measuring devices such as blood glucose measuring devices, therapeutic devices or administration devices, such as insulin pumps or insulin pens, and intelligent facilities for display and analysis on the other side, such as palm tops or computers. It thus contributes to a "circle of care" that includes three core areas, namely the area of "collect-and-monitor" being the capturing of measuring values and data (e.g. blood glucose values, ingestions of food, exercises, fat values, HbA1c, foot and eye examinations, administration of medications, blood pressure), the area of "analyze-and-advise" being analysis and recommendation (e.g. bolus recommendation, generation of reports, risk and potential reports), and the area of "act" being acting and, in the case of diabetic disease, insulin administration including optimization of therapy. With regard to diabetic diseases, this includes blood glucose measuring devices, data processing device such as the communication adapter 6, and insulin administration facilities.

It is noted that terms like "preferably", "commonly", and "typically" are not utilized herein to limit the scope of the claimed invention or to imply that certain features are critical, essential or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A communication adapter for a portable, ambulant-operable medical device for diagnosis or treatment of a disorder of glucose metabolism, the communication adapter processing data between the medical device and a computer that serves for displaying operating parameters or measuring data of the medical device and/or for operating the medical device, comprising:
   the medical device comprises,
     a device processor for controlling the device, and
     a device-adapter interface for the communication of the device processor with a communication adapter, and
   the communication adapter comprises,
     an adapter processor for controlling the communication adapter,
     an adapter-device interface for the communication of the communication adapter with the medical device,
     an adapter-computer interface for the communication of the adapter processor with a computer interface of the computer, and
     a device driver with corresponding transmission protocol for the communication with the device,
   and wherein
     the communication adapter comprises a software or firmware that performs data analysis of a data read-out from the medical device independent of the computer, the communications adapter temporarily stores the data read-out from the device, and the data adapter provides the data that had been analyzed in a data format that is displayed by the computer with standard display software.

2. A communication adapter for a portable, ambulant-operable medical device for diagnosis or treatment of a disorder of glucose metabolism, the communications adapter, processing data between the medical device and a computer that serves for displaying operating parameters or measuring data of the medical device and/or operating the medical device, comprising:
   wherein the medical device comprises,
     a device processor for controlling the device, and
     a device-adapter interface for the communication of the device processor with a communication adapter, and
   wherein the communication adapter comprises,
     an adapter processor for controlling the communication adapter,
     an adapter-device interface for the communication of the communication adapter with the medical device,
     an adapter-computer interface for the communication of the adapter processor with a computer interface of the computer, and
     a device driver with corresponding transmission protocol for the communication with the device,
   wherein
     control of the communication adapter by the computer is implemented by sending read commands from the computer to the communication adapter by means of which trigger files in the communication adapter are read that are interpreted as control commands for the communication adapter by a software or firmware of the communication adapter.

3. The communication adapter according to claim 1, wherein the adapter-device interface for the communication of the communication adapter with the device is an interface for wireless data transmission.

4. The communication adapter according to claim 1, wherein the adapter-computer interface for the communication of the adapter processor with the computer interface of the computer is an interface for wire-based data transmission.

5. The communication adapter according to claim 1, wherein the wire-based adapter-computer interface is a serial interface, a parallel interface, a firewire interface, or a universal serial bus interface.

6. The communication adapter according claim 1, wherein the communications adapter further comprises a plurality of device drivers with corresponding transmission protocols that are automatically queried in the case of a device communicating with the communication adapter via the adapter-device interface in order to select from the plurality of device drivers an adequate device driver for the device on hand.

7. The communication adapter according to claim 1, wherein the data format generated by the communication adapter is a format that can be displayed by an Internet browser or an hypertext markup language (HTML) or extensible markup language (XML) format that can be displayed with HTML or XML display software.

8. The communication adapter according to claim 1, wherein the communication adapter, in addition, generates the data read-out from the device in a data format that can be stored and stores this data in at least one file in the communication adapter from where it can be read-out by the computer via the adapter-computer interface.

9. The communication adapter according to claim 1, wherein the adapter comprises no intrinsic or internal power supply and is supplied with power from the computer via the adapter-computer interface.

10. The communication adapter according to claim 1, wherein the communications adapter is provided for programming of the device from the computer, whereby the programming of the device from the computer proceeds via the computer interface of the computer to the communication adapter and from the communication adapter via the adapter-device interface of the communication adapter to the device.

11. The communication adapter according to claim 1, wherein the device is an analytical measuring device that determines or records medical parameter, in particular a blood glucose meter, a cholesterol measuring device, a blood coagulation parameter measuring device, a blood pressure measuring device, a device for measuring the body weight, a blood glucose recorder or a blood pressure recorder or a device for injection of a medical agent into a body.

12. The communication adapter according to claim 1, wherein the device and the communication adapter transmit operating data or measuring values from the device via the communication adapter to the computer, whereby the operating data or measuring values are time points in the past.

13. A system for operating a portable, ambulant-operable medical device for diagnosis or treatment of a disorder of glucose metabolism, with a data transmission between the medical device and a computer that serves for displaying operating parameters or measuring data of the device and/or for operating the device, characterized in that it comprises a communication adapter according to claim 1 and at least one medical device with a device processor that controls the device and with a device-adapter interface for the communication of the device processor with a communication adapter.

14. The system according to claim 13, characterized in that the medical device is a device that can be operated independently of the communication adapter.

15. The system according to claim 13 wherein the medical device is an analytical measuring device that determines or records a medically significant parameter that is used for diagnosis or treatment of disorders of glucose metabolism, in particular a blood glucose measuring device, a blood sugar measuring device or a blood glucose recorder, a cholesterol measuring device, a device for measuring a blood coagulation parameter, a blood pressure measuring device, a blood pressure recorder, a device for measuring the body weight or a device for injection of a medical agent into a body, in particular an insulin pump.

16. The system according to claim 13, wherein the display software is a software that can read the data to be displayed from the communication adapter, but cannot change this data on the communication adapter or the device, wherein a data read-out from the device by the computer are transmitted to the computer to be displayed temporarily and the display software reads-out the data from the device but cannot delete or change that data on the communication adapter or on the device the data remaining on the communication adapter and/or the data remaining on the device, respectively.

17. A communications adapter for an ambulant medical device, comprising:
 a housing containing electronics comprising,
  a processor, and
  memory coupled to the processor;
 a computer interface coupled to the electronics, the computer interface configured coupleable to a computer port to transmit data, receive data, and supply power to the electronics;
 a medical device interface coupled to the electronics, the medical device interface operable to communicate with a medical device to transmit data and receive data;
 device drivers present in the memory, each device driver having a communications protocol to permit reception of data from one or more medical devices and transmission of data to one or more medical devices;
 processing software present in the memory to processes the data received from one or more medical devices into a report; and
 reporting software present in the memory to configure the report on an internet browser operating on a computer free from further processing by the computer.

18. The communications adapter in claim 17 wherein the medical device received data is stored in the memory and not on a computer thereby increasing data security by avoiding storing medical device received data on the computer connected to the communications adapter.

19. The communications adapter in claim 17 wherein the computer is free from having programs that process medical device received data, the computer serving as a user interface for displaying the report and operating the communications adapter.

20. The communications adapter in claim 17 wherein the reporting software creates the report as HTML data that is display on the internet browser.

21. The communications adapter in claim 17, further comprising,
 a trigger file contained in the memory that is executed when the computer sends a read command to the computer interface that the processor interprets as a execution command to control the communications adapter.

22. The communications adapter in claim 21 wherein the trigger file comprises a plurality of trigger files are located in more than one directory contained in the memory to increase the complexity of the execution command.

23. The communications adapter in claim 17 further comprising,
 a driver selector present in the memory, wherein the driver selector attempts to receive data through one or more device drivers until a compatible device driver is selected to permit receiving and transmitting data between the medical device and the medical device interface.

24. The communications adapter in claim 17, wherein the medical device is selected from the group consisting of a blood glucose meter, an insulin pump, an insulin pen, a cholesterol measuring device, a blood coagulation parameter measuring device, a blood pressure measuring device, a device for measuring the body weight, a blood glucose recorder, and a blood pressure recorder.

25. A communications adapter for an ambulant medical device, comprising:
 a housing containing electronics comprising
  a processor, and
  memory coupled to the processor;
 a computer interface coupled to the electronics, the computer interface configured coupleable to a computer port to transmit data, receive data, and supply power to the electronics;
 a medical device interface coupled to the electronic, the medical device interface operable to communicate with a medical device to transmit and receive data;
 device drivers contained in the memory, each device driver having a communications protocol to permit reception of data from one or more medical devices and transmission of data to one or more medical devices;
 a driver selector present in the memory, wherein the driver selector attempts to receive data through one or more of the device drivers until a compatible device driver is selected to permit receiving and transmitting data between the medical device and the medical device interface;
 means for processing the data received from one or more medical devices into a report; and reporting software present in memory to create the report that is displayed on an internet browser operating on a computer free from further processing by the computer.

26. A communications adapter for an ambulant medical device, comprising:
a housing containing electronics comprising,
a processor, and
memory coupled to the processor;
a computer interface coupled to the electronics, the computer interface configured coupleable to a computer port to transmit data, receive data, and supply power to the electronics;
a medical device interface coupled to the electronic, the medical device interface operable to communicate with a medical device to transmit and receive data;
device drivers present in the memory, each device driver having a communications protocol to permit reception of data from one or more medical devices and transmission of data to one or more medical devices;
a driver selector contained in the memory, wherein the driver selector attempts to receive data through one or more of the device drivers until a compatible device driver is selected to permit receiving and transmitting data between the medical device and the medical device interface;
processing software contained in memory to processes the data received from one or more medical devices into a report; and
means for reporting that creates the report that is displayed on an internet browser operating on a computer free from further processing by the computer.

27. A method for interfacing a medical device with a computer without the computer storing medical device files or having programs to analyze data received from a medical device, comprising:
transmitting data from a medical device to a communications adapter;
receiving the data by the communications adapter that was transmitted by the medical device;
selecting a device driver by the communications adapter that is compatible with the medical device;
adjusting the medical device transmission rate by the communications adapter to an optimal rate;
storing medical device data in memory present in the communications adapter;
analyzing the medical device data in the communications adapter to produce a report without processing by a computer;
sending the report from the communications adapter to the computer; and
reporting the report on an internet browser operating on the computer.

28. The method in 27 further comprising,
sending a read command from the computer to the communications adapter to select a trigger file contained in the communications adapter that the communications adapter interprets as an execution command to control the communications adapter.

29. The method in claim 28 wherein there is a plurality of trigger files located in more than one directory present in memory so that upon receiving a read file from the computer the trigger files are executed to increase the complexity of the execution command.

30. The method in claim 27 wherein the medical device data is stored in the communications adapter increasing data security by avoiding storing medical device received data on the computer.

31. The method in claim 27 wherein the computer is free from having programs that process the medical device received data, the computer serving as a user interface for displaying the report and operating the communications adapter.

32. The method in claim 27 wherein the report is sent from the communications adapter to the computer as HTML data.

33. The method as in claim 27 wherein the medical device comprises a first medical device and a second medical device that transmit data simultaneously to the communications adapter and the communications adapter upon receiving the data selects a driver for the first medical device and selects another driver for the second medical to receive the data transmitted simultaneously from the first medical device and the second medical device.

34. The method in claim 27 wherein the medical device is selected from the group consisting of a blood glucose meter, an insulin pump, an insulin pen, a cholesterol measuring device, a blood coagulation parameter measuring device, a blood pressure measuring device, a device for measuring the body weight, a blood glucose recorder, and a blood pressure recorder.

35. The communication adapter according to claim 3, wherein the interface for wireless data transmission comprises an infrared interface or a radio interface.

36. The communication adapter according to claim 11, wherein the device for injection of a medical agent into a body comprises an insulin pump.

* * * * *